United States Patent [19]

Hamunen

[11] 4,420,427

[45] Dec. 13, 1983

[54] PROCESS FOR THE SEPARATION OF STEROLS OR MIXTURES OF STEROLS

[75] Inventor: Antti Hamunen, Lappeenranta, Finland

[73] Assignee: OY Kaukus AB, Lappeenranta, Finland

[21] Appl. No.: 396,336

[22] Filed: Jul. 8, 1982

[30] Foreign Application Priority Data

Jul. 21, 1981 [FI] Finland .................................. 812278

[51] Int. Cl.$^3$ .............................................. C07J 9/00
[52] U.S. Cl. .............................................. 260/397.25
[58] Field of Search .................................. 260/397.25

[56] References Cited

U.S. PATENT DOCUMENTS 2,839,544  6/1958  Greiner et al. ................. 260/397.25
4,153,622  5/1979  Lamminkari et al. ......... 260/397.25

*Primary Examiner*—Elbert L. Roberts
*Attorney, Agent, or Firm*—Scully, Scott, Murphy & Presser

[57] ABSTRACT

The invention relates to a process for the isolation of sterols or sterol mixtures from unsaponifiable fractions of extractants of vegetable origin, especially from the neutral substance of crude soap from the sulphate cellulose process. According to the process, the neutral substance and a small amount of a suitable solvent which, depending on the desired composition of the product, preferably is methanol or a mixture of methyl ethyl ketone, are mixed, when required, while heating, the cooled mixture is filtered and the sterol precipitate obtained is washed with a suitable wash solvent, preferably acetone or a mixture of acetone and methanol. The sterol mixture prepared according to the invention and obtained when starting out from the unsaponifiables of crude soap obtained from raw wood comprising birch and using methanol as solvent contains about 5% campesterol, 65 to 80% β-sitosterol and 15 to 25% α-sitosterol. When using a mixture of methyl ethyl ketone and water as solvent, a product is obtained having a low α-sitosterol content (<5%), a campesterol content of 6 to 8% and a β-sitosterol content of 85 to 90%.

10 Claims, No Drawings

PROCESS FOR THE SEPARATION OF STEROLS OR MIXTURES OF STEROLS

The present invention relates to a process for the separation of one or more sterols or mixtures of sterols.

By means of the process according to the invention it is possible to prepare technical β-sitosterol which, as such, can be used in the cosmetic industry and which, when refined, is useful for pharmaceutical purposes and for the preparation of steroid intermediates.

The patent literature describes some processes for the isolation of sitosterols from sterol-containing sources.

U.S. Pat. No. 2,835,682 discloses a process according to which sterols are extracted with gaseous hydrogarbon, the so obtained sterol-rich fraction is saponified in an alcoholic solution and the sterols are crystallized by adding water and by cooling.

U.S. Pat. No. 2,866,797 describes a process for the isolation of sterols from unsaponifiable fractions of vegetable origin. In the process, the sterols are crystallized from an ethylene dichloride extract of the unsaponifiable material by adding small amounts of water and methanol.

U.S. Pat. No. 3,691,211 describes a process according to which the sterols can be isolated from sterol esters of vegetable origin, for example, tall oil pitch. The process comprises a water/alcohol/hydrocarbon extraction, saponification and crystallization.

According to Finnish Pat. No. 56 969 a sterol mixture is isolated from sterol-containing material by means of a liquid/liquid extraction. The sterols are extracted into a hydrophilic alcoholic phase from which they are crystallized by concentrating the solution and by cooling.

Finnish Pat. No. 57 956 describes a process according to which relatively pure β-sitosterol can be isolated from the unsaponifiables of crude soap. The process comprises treatment of the unsaponifiables with a strong acid and crystallization of sitosterol from a suitable organic solvent.

As compared to the processes described above, the process according to the invention is simple and, due to the small amounts of solvent required, economical also when carried out on a large scale. Unsaponifiables of crude soap obtainable from the sulphate cellulose process, the so-called neutral substance comprising unsaponifiable neutral components of pulpwood, especially birch and pine, have been used as starting material in the invention. The neutral substance contains about 10 to 13% β-sitosterol and campesterol, about 5% α-sitosterol, about 5% squalene, and about 20% betulaprenols.

The invention is characterized by (a) adding to the sterol-containing fraction a solvent comprising methanol or ethanol or a mixture thereof or a mixture of methyl ethyl ketone and water containing more than 5% by weight of water, in a weight ratio sterol-containing material:solvent = 1:0.2 to 1:20, preferably 1:1, (b) mixing the mixture of solvent and sterol-containing fraction at room temperature, heating said mixture, when required for dissolving undesired neutral substance components and cooling to room temperature or below it, (c) filtering the precipitated sitosterol, and (d) removing the non-sterolic components in the sitosterol precipitate by washing the precipitate with a suitable solvent, preferably acetone or a mixture of acetone and methanol having an acetone content of >10%.

After step (b), the product contains as impurity about 25% by weight of non-sterolic components of the neutral substance, for example, betulaprenols and squalene.

The composition of the sterol mixture prepared by means of the process according to the invention depends on the crystallization solvent/solvent mixture to be used. Suitable crystallization solvents are lower alcohols, especially methanol and a mixture of methyl ethyl ketone and water. If methanol is used as solvent, the sitosterol mixture obtained will, in addition to campesterol (4 to 5%) and β-sitosterol (65 to 75%), contain 15 to 25% α-sitosterol. Such a sterol mixture is as such useful in the cosmetic industry and it may, for example, by fractional crystallization be purified to α-sitosterol free of β-sitosterol which is suitable for pharmaceutical purposes and as raw material for steroid intermediates. However, when aiming at pure β-sitosterol, it is preferable to use a mixture of methyl ethyl ketone and water as solvent. The α-sitosterol content of the product then obtained is low (<5%) due to which an economical purification of the product, for example, by crystallization presents no difficulties. The amount of water should be more than 5% by weight of the amount of methyl ethyl ketone because, otherwise, along with sitosterol, betulin will be crystallized which in pharmaceutical applications is an undesired substance and, in general, difficult to remove by crystallization. At low water contents also the yield of sitosterol remains low.

As wash solvent for the sterol-containing precipitate it is preferred to use a solvent or solvent mixture in which sitosterol dissolves poorly but impurities, such as betula prenols and squalene, dissolve easily. Solvents meeting these requirements comprise acetone and, especially, a mixture of methanol and acetone having an acetone content of more than 10%.

The examples in the following table illustrate the invention. The solvent was added to the mixture of unsaponifiables obtained from crude soap skimmings (25 g) and the mixture was boiled 5 to 10 minutes, whereafter the mixture was cooled to +15° C. in a thermostated water bath while stirring lightly. The sitosterol was filtered, and the precipitate washed with 3×10 ml of acetone.

TABLE 1

Crystallization of sitosterol from neutral substance

| Experiment No. | Solvent | Amount of solvent (g) | Crystallization yield % of neutral substance | Impurities % of crystallization precipitate α-sitosterol | betulin |
|---|---|---|---|---|---|
| 1 | MeOH | 10 | 10.7 | 20–25 | <0.5 |
| 2 | " | 20 | 11.5 | " | " |
| 3 | " | 30 | 13.5 | " | " |
| 4 | " | 40 | 10.2 | " | " |
| 5 | EtOH | 25 | 3.3 | " | " |
| 6 | EtOH:MeOH 1:1 | 25 | 7.5 | " | " |
| 7 | MEK | 30 | 3.1 | 6.5 | 42 |
| 8 | MEK:H$_2$O 97:3 | 30 | 3.6 | 5 | 20 |
| 9 | MEK:H$_2$O 95:5 | 30 | 4.7 | 3 | 2 |
| 10 | MEK:H$_2$O 90:10 | 30 | 6.7 | 3 | — |
| 11 | MEK:H$_2$O 80:10 | 30 | 5.0 | 2 | — |
| 12* | MEOH | 25 | 10.3 | 23 | 3 |

TABLE 1-continued

Crystallization of sitosterol from neutral substance

| Experiment No. | Solvent | Amount of solvent (g) | Crystallization yield % of neutral substance | Impurities % of crystallization precipitate α-sitosterol | betulin |
|---|---|---|---|---|---|
| 13** | NEOH | 25 | 12.1 | 24 | — |

*The neutral substance and methanol were mixed without heating at room temperature for ½ h, whereafter the mixture was filtered and washed with acetone.
**Wash with 3 × 10 ml of a (1:1) mixture of acetone and methanol.

What I claim is:

1. A process for the separation of one or more sterols or mixtures of sterols selectively from sterol-containing unsaponifiable material obtained from sulphate soap, saponifiable vegetable oils, tall oil or any other material of vegetable origin, comprising the steps of:
   (a) adding to the sterol-containing fraction a solvent selected from the group consisting of methanol, ethanol, a mixture of methanol and ethanol, and a mixture of methyl ethyl ketone and water containing more than 5% by weight of water, wherein the weight ratio of sterol-containing material:solvent = 1:0.2 to 1:20,
   (b) mixing the mixture of solvent and sterol-containing fraction at room temperature, heating said mixture, when required, for dissolving undesired neutral components and cooling to room temperature or below it,
   (c) filtering precipitated sitosterol, and
   (d) removing the non-sterolic components in the sitosterol precipitate by washing the precipitate with a suitable solvent.

2. A process according to claim 1, wherein the solvent is methanol.

3. A process according to claim 1, wherein the solvent is a mixture of methyl ethyl ketone and water containing more than 5% by weight of water.

4. A process according to claim 1, wherein the weight ratio of sterol-containing material:solvent = about 1:1.

5. A process according to claim 1, wherein the solvent used to wash the precipitate is acetone or a mixture of acetone and methanol having an acetone content of about 10%.

6. A process for the selective separation of one or more sterols or mixtures of sterols from sterol-containing unsaponifiable material obtained from sulphate soap, saponifiable vegetable oils, tall oils or other material of vegetable origin, consisting essentially of the steps of:
   (a) adding to the sterol-containing fraction of unsaponifiable material a solvent selected from the group consisting of methanol, ethanol, a mixture of methanol and ethanol, or a mixture of methyl ethyl ketone and water containing more than 5% by weight of water, wherein the weight ratio of sterol-containing material:solvent = 1:0.2 to 1:20,
   (b) mixing the mixture of solvent and sterol-containing fraction at room temperature, heating said mixture, when required, for dissolving undesired neutral components and cooling to room temperature or below it,
   (c) filtering precipitated sitosterol, and
   (d) removing the non-sterolic components in the sitosterol precipitate by washing the precipitate with a solvent suitable for said washing.

7. A process according to claim 6, wherein the solvent is methanol.

8. A process according to claim 6, wherein the solvent is a mixture of methyl ethyl ketone and water containing more than 5% by weight of water.

9. A process according to claim 6, wherein the weight ratio of sterol-containing material:solvent = about 1:1.

10. A process according to claim 6, wherein the solvent used to wash the precipitate is acetone or a mixture of acetone and methanol having an acetone content of about 10%.

* * * * *